US005909733A

United States Patent [19]

Ehrich

[11] Patent Number: 5,909,733

[45] Date of Patent: Jun. 8, 1999

[54] MECHANISM FOR SECURING A PATIENT'S LIMB

[76] Inventor: Keith Ehrich, 111 Mays Rd., Milledgeville, Ga. 31061

[21] Appl. No.: 09/121,150

[22] Filed: Jul. 23, 1998

[51] Int. Cl.$^{6}$ .......... A61B 19/00

[52] U.S. Cl. .......... 128/869; 128/878; 5/624

[58] Field of Search .......... 128/845, 846, 128/869, 877, 878, 879, 882; 602/32–40; 5/621, 624, 630, 648

[56] References Cited

U.S. PATENT DOCUMENTS

| | | | |
|---|---|---|---|
| 2,679,842 | 6/1954 | Brill . | |
| 4,515,155 | 5/1985 | Wagemann . | |
| 4,526,165 | 7/1985 | Mielnik, Jr. et al. . | |
| 4,526,355 | 7/1985 | Moore | 5/624 |
| 4,545,573 | 10/1985 | Murphy | 5/624 |
| 4,549,540 | 10/1985 | Caspari et al. . | |
| 4,624,245 | 11/1986 | Mullin | 5/621 |
| 4,662,366 | 5/1987 | Tari . | |
| 4,717,133 | 1/1988 | Walsh | 5/624 |
| 4,729,138 | 3/1988 | Heyman et al. . | |
| 4,766,892 | 8/1988 | Kreitman . | |
| 5,390,383 | 2/1995 | Carn | 5/621 |
| 5,549,121 | 8/1996 | Vinci . | |

*Primary Examiner*—Michael A. Brown
*Attorney, Agent, or Firm*—Hinkle & Associates, P.C.

[57] ABSTRACT

An adjustable limb restraint mechanism (11) easily attachable to human medical transporting devices to rigidly support a limb (15) of a patient. The limb restraint mechanism has a pad surface (13) for support of the limb, and an adjustable mechanism (14) which allows the restraint mechanism structure to be attached to side rails of the transporting structure so that medical technicians may immobilize a patient's limb to the restraint mechanism for purposes such as performing interveneous injections.

8 Claims, 2 Drawing Sheets

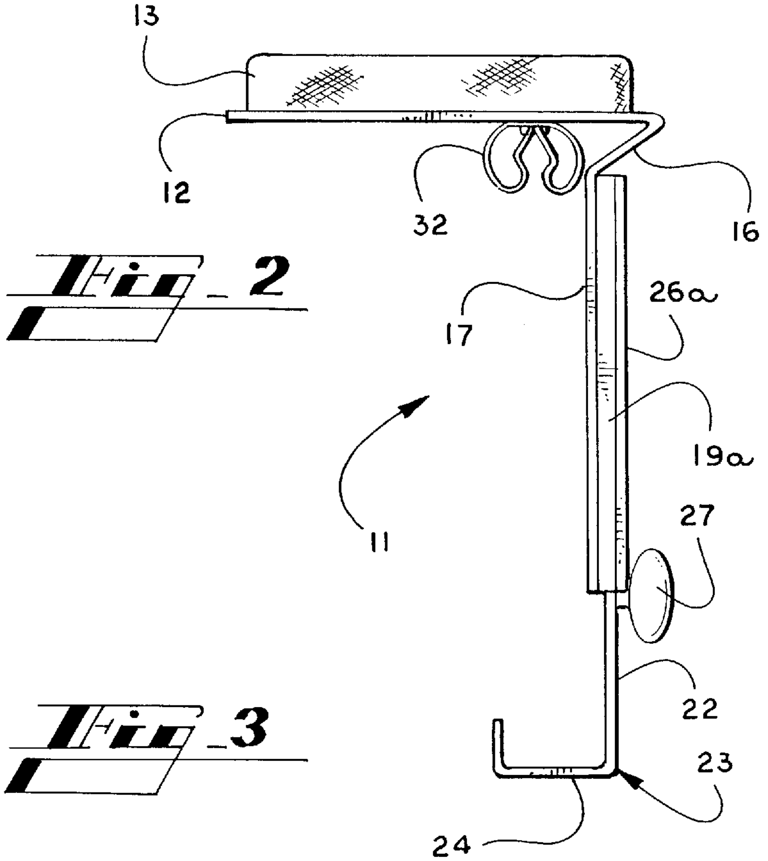
Fig_2
Fig_3
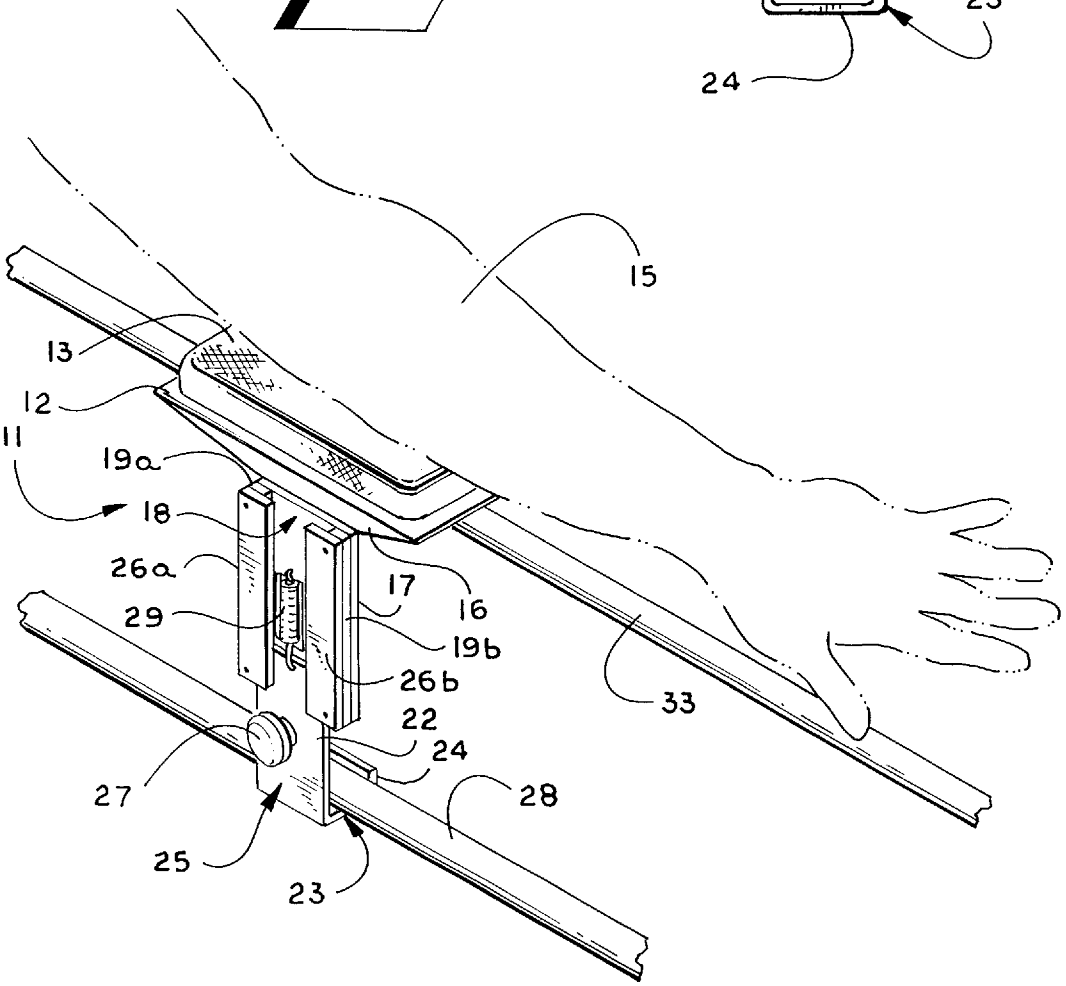

MECHANISM FOR SECURING A PATIENT'S LIMB

BACKGROUND OF THE INVENTION

1. Field of the Invention

The present invention relates generally to positioning devices for use in the medical profession to restrain a patient's limb to a supporting restraint mechanism. The invention is so constructed that it is applicable to many types of patient transporters currently used in hospitals and ambulances.

2. Description of the Related Art

It is common in the medical environment to provide limb restraints, especially during medical procedures. In the past, many types of limb restraints have been used with a certain amount of success.

Many limb restraints of the prior art are generally fixed to a bed or to a table, especially if the restraint is to be used in association with orthopedic examinations or manipulations of the patient's limb. These types of restraint mechanisms are not easily used in a variety of settings and cannot be easily utilized with beds, tables, stretchers or gurneys which are transportable.

For instance, a restraint clamp is described in U.S. Pat. No. 4,729,138 issued to Heyman et al. which shows an adjustable utility clamp device attachable to a hospital bed frame, or to a standard bed tubular frame member, which allows for easy securing and release of the restraint at desired times. However, this particular device is not applicable to procedures where it is desired to maintain the patient's limb in a stable non-moving situation, especially when it is desired to give the patient an interveneous injection of some sort.

In U.S. Pat. No. 4,766,892 issued to Kreitman, a fixed type of restraint is shown for utilization especially with orthopedic examinations and manipulations. The particular frame shown in this patent is a rigid frame and, while it may be adjustable with respect to the table with which it is to be used, it is not easily utilizable with transportable devices which transport patients. This particular device shown by Kreitman especially does not have a planar surface to which the limb may be strapped.

Other restraint mechanisms which can be used with portable patient transporters typically are not easily used with a variety of types of transporters, or they do not rigidly support the limb of the patient. For example, U.S. Pat. No. 2,679,842 issued to Brill discloses a restraining mechanism attached to a hospital bed. The purpose of the device of this patent is to prevent the patient from moving the limbs and to maintain the patient in a supine position. The restraint is flexible and does not limit all motion of the limbs, but generally restrains a patient to a limited movement area.

SUMMARY OF THE INVENTION

In accordance with the present invention and the contemplated problems that have existed and continue to exist in this field, the present invention provides a limb restraint mechanism which has an object to provide stable support to a patient's limb when the device is used on a patient transporter so that the patient's limb may be secured to the limb restraint for such purposes as an interveneous procedure upon the patient.

Another object is to provide a patient limb restraint which is easily used on multiple types of patient transporters such as beds, tables, stretchers or gurneys.

Yet another object of the invention is to provide a patient restraint mechanism which is simple to use and is inexpensive, and yet maintains the patient's limb securely and safely to the limb restraint mechanism so that standard medical procedures may be utilized.

This invention accomplishes the above and other objects by use of an easily attachable and removable restraint mechanism which may be commonly attached to bed rails or other tubular types of rails associated with hospital beds, table stretchers or gurneys which typically are portable or movable. The invention herein is particularly designed to fit upon the typical type of stretcher which is used in emergency vehicles so that the patient who is lying on the stretcher could have his/her arm strapped to an arm board for the purposes of maintaining the arm in a stable, secure relationship while the patient is in route to the hospital in order for the emergency personnel to keep I.V. drips going into the limb. This particular invention is designed so that the arm is attached to a limb pad placed upon a restraint plate such that the arm may be secured thereto by any suitable quick release means such as straps with hook and loop fasteners. The restraint plate will have clips on the underside thereof for the purpose of snapping around the tubular structure of the stretcher or other transportable device, and will be further attached to preferably a second tubular structure remote from the first tubular support by means of a J-type clamp which is adjustable with respect to the restraint plate so that it may clamp around the lower tubular support and be firmly engaged therewith to provide lateral and rotational stabilization to the restraint plate. Depending upon the type of stretcher or gurney transportable device utilized, there may be some difference in the distance between an upper tubular support member and a lower tubular support member and, therefore, the clamping portion of the present invention is spring loaded so that the medical technician may adjust the clamping portion to the frame of the transport device and interlock it thereto to provide a stable relationship with respect to the transport device.

Other objects, advantages and capabilities of the invention will become apparent from the following description taken in conjunction with the accompanying drawings showing a preferred embodiment of the invention.

BRIEF DESCRIPTION OF THE DRAWINGS

FIG. 2 is a side elevation view of the restraint mechanism, and

FIG. 3 is an overall perspective view of the restraint mechanism shown mounted on a transport device with a patient's arm resting upon the limb pad of the restraint mechanism.

DESCRIPTION OF THE PREFERRED EMBODIMENT

Figure 1:
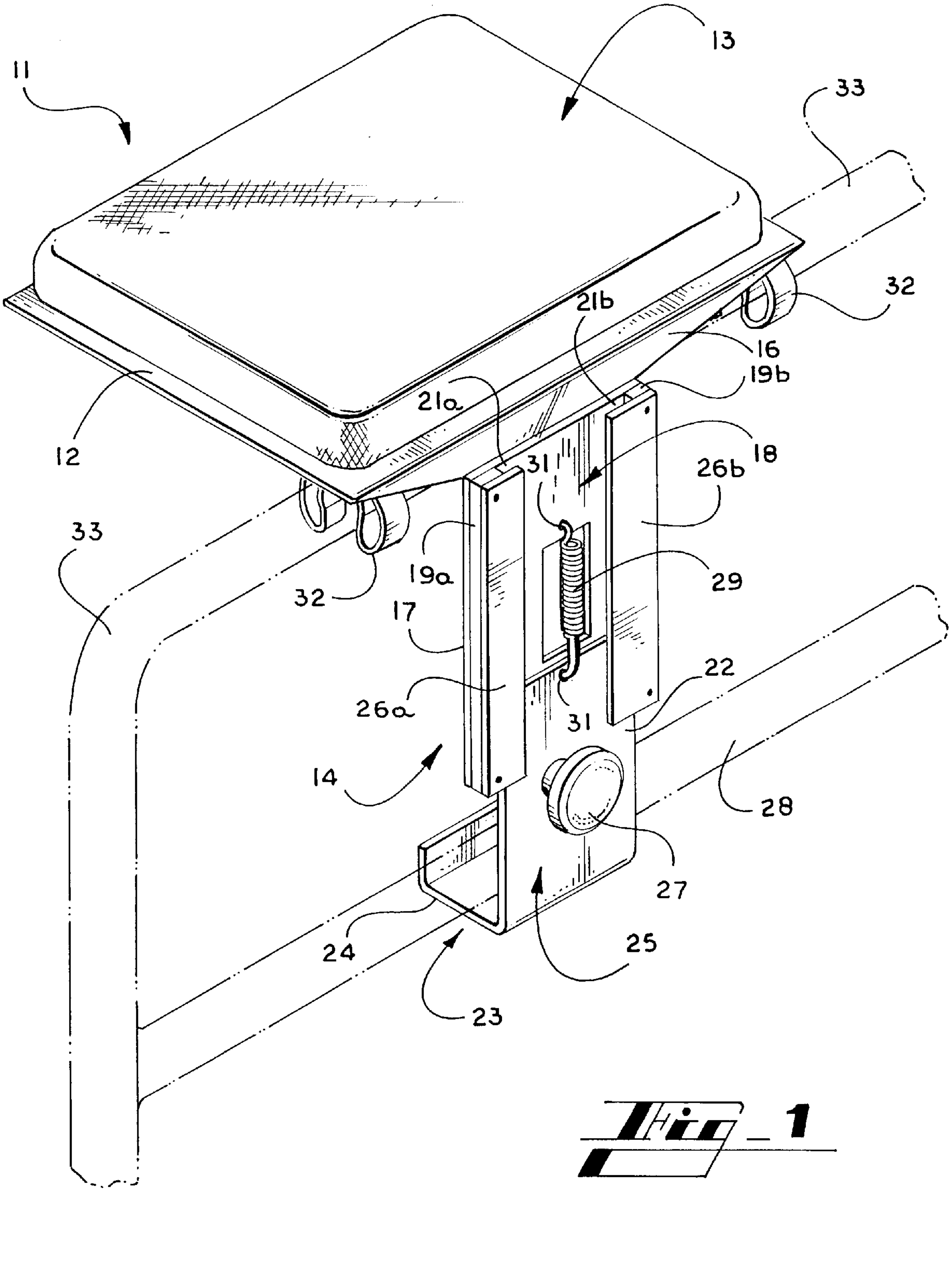
FIG. 1 is an overall perspective view of a restraint system shown mounted on tubular support members of a transport device.

Referring to the drawings wherein like reference numerals designate corresponding parts throughout the several figures, the restraint mechanism of the present invention is indicated by the numeral 11. Major sub-assemblies of the restraint mechanism 11 comprise a restraint plate 12, a limb pad 13 and an adjustable clamp assembly 14. Referring to FIG. 1, the limb pad 13 is suitably attached to the restraint plate 12 by a suitable adhesive or by fasteners between the limb pad 13 and the restraint plate 12. While in the drawings, the restraint plate and the limb pad are shown as being generally rectangular. It may well be that, in actual use, both would be configured more to the general shape of a patient's arm or leg as opposed to the configuration shown herein. The configuration shown in the drawings is for illustrative purposes only and one skilled in the art may very well decide that a different configuration might be utilized for a particular purpose when securing a patient's limb thereto. Further, in FIG. 3, a patient's arm 15 is shown in phantom lines resting upon the limb pad 13. Again, the representation of the arm is for illustrative purposes only and, in order to not obscure the drawings in any way, typical restraint devices such as a strap with hook and loop fasteners or any other type of fastening device is not shown, but it should be obvious that various types of restraints could be utilized herein in virtually any configuration which the medical technician desires to use.

Referring to all of the figures, it is seen that the restraint plate is of generally planar configuration to support the limb pad 13, but has a reentrant lip 16 connected to the upper slide plate assembly 18 which forms a part of the adjustable clamp assembly 14.

The upper slide plate assembly 18 comprises an elongated upper plate 17 and a pair of spacers 19*a* and 19*b* which define a pair of slide slots 21*a* and 21*b* into which the lower movable slide plate 22 is fitted in order to reciprocate upwardly and downwardly for purposes to be described.

At the lower end of the adjustable clamp assembly 14, there is a J-shaped clamping member 23 comprising a clamp 24 which is the operative part of the lower slide plate assembly 25. The slide plate 22 is designed to rest in and reciprocate within the slide slots 21*a* and 21*b* as more particular shown in FIG. 1. To fully define the slide slots 21*a* and 21*b*, there are a pair of parallel slide plates 26*a*, 26*b* which are attached to respective spacers 19*a* and 19b. Therefore, the combination of the upper plate member 17, along with spacers 19*a*, 19*b* and with the parallel slide plates 26*a* and 26*b*, form the slide slots 21*a* and 21*b* into which the lower movable slide plate 22 is capable of reciprocative motion. The lower slide plate 22 is loosely retained within the slide slots 21*a* and 21*b* until it is utilized in its intended manner. Once the restraint mechanism is utilized in its intended manner, the lower movable slide plate 22 is moved distally with respect to the clamp assembly 14 by means of the adjusting knob 27 so that the clamping member 23 will fit around a lower support member, which in this case is shown as a tubular support 28. As specifically seen in FIGS. 1 and 3, the J-shaped clamping member 23 will be pulled downwardly past the tubular support 28 and then firmly engaged to the bottom surface thereof to maintain the restraint mechanism with respect to the lower tubular support. In order to apply sufficient pressure to maintain the unit in its intended position, a spring 29 is affixed between the upper portion of the lower movable slide plate 22 and a suitable position in the upper plate 17. The opposite ends of spring 29 are shown affixed in the respective mounting holes 31.

In order to fully stabilize the restraint mechanism 11, the restraint plate 12 has positioned to the underside thereof clamps 32 which are suitably affixed to an upper tubular support 33. With respect to the tubular supports 28 and 33, it should be noted that the present invention could very well be connected to other members that are not necessarily circular in a cross-section. However, in the usual mode of use in the present invention, it is contemplated that the restraint mechanism herein would very commonly be used with ambulance stretchers and hospital gurneys which typically have tubular supports. In addition, clamps 32 are shown to be of a spring clip arrangement and such clamps could well be a J-shaped clamping member, such as is shown on the lower movable slide plate 25 and such would equally stabilize the restraint mechanism to an upper tubular support 33.

To utilize the present invention, a medical technician, such as a paramedic in an ambulance, would position the restraint mechanism 11 to the stretcher assembly by placing the restraint plate 12 over the upper tubular support 33 so that the clamps 32 will be in firm contact therewith, and then would pull down on the lower movable slide plate 22, preferably with the adjusting knob 27, so that the J-shaped clamping member 23 clears the lower tubular support 28 and then would place the reentrant portion of the clamping member 23 around the tubular support 28 and release the slide plate 22 so that the spring 29 would reciprocate the slide plate 22 upwardly toward the restraint plate, thereby firmly clamping the restraint mechanism 11 to both of tubular supports 28 and 33. Once this has been accomplished, the medical technician would take a patient's limb, in most cases it would be an arm, place it upon the limb pad 13 and strap the arm down to the limb pad with suitable strapping members so that the arm would be immobilized. Once the arm has been immobilized, the medical technician would typically put some sort of an interveneous drip into the arm pursuant to normal medical procedures. Again, it would be well within the scope of this invention to configure the restraint plate 12 and the limb pad 13 to such configurations which would be applicable for the intended use. For instance, the restraint plate 12 and the limb pad 13 might be elongated substantially in order to more nearly fit a supine arm.

Therefore, the foregoing is considered as illustrative only of the principles of the invention. Further, various modifications may be made of the invention without departing from the scope thereof and it is desired, therefore, that only such limitations shall be placed thereon as are imposed by the prior art and which are set forth in the appended claims.

What is claimed is:

1. A limb restraining mechanism for use in combination with a patient transporter, wherein the transporter has upper and lower support members, the restraining mechanism comprising:

a restraint plate and a limb pad assembly and an adjustable clamp assembly adapted to be affixed to the upper and lower support members of the patient transporter;

the restraint plate having a top planar surface to which the limb pad is affixed, and the restraint plate further having a proximal edge surface from which depends the adjustable clamp assembly;

the restraint plate having a bottom planar surface to which at least one clamp is attached;

the adjustable clamp assembly comprising an upper slide plate assembly and a lower slide plate assembly, the upper slide plate assembly being a thin elongated plate having a proximal end and a distal end wherein the proximal end is attached to and depends from the proximal edge surface of the restraint plate, the lower slide plate assembly being a thin elongated plate having a proximal end and a distal end wherein the proximal end is juxtaposed to the upper slide plate assembly in a sliding relationship; and the lower slide plate assembly having its distal end terminating in a clamp assembly.

2. A limb restraining mechanism as claimed in claim 1, wherein the adjustable clamp assembly further comprises track means to enclose a portion of the lower slide plate assembly and to maintain the lower slide plate assembly juxtaposed with the upper slide plate assembly.

3. A limb restraining mechanism as claimed in claim 2, wherein the upper slide plate assembly has a first planar surface and oppositely disposed side edges flanking the first planar surface, the track means further having oppositely disposed slot plates mounted adjacent to each side edge of the upper slide plate such that the slot plates define a slide slot therebetween.

4. A limb restraining mechanism as claimed in claim 3, wherein the lower slide plate is received within the slide slot formed by the slot plates.

5. A limb restraining mechanism as claimed in claim 3, wherein the lower slide plate has a first planar surface and oppositely disposed side edges flanking the first planar surface, the lower slide plate being received within the slide slot formed by the slot plates to form a sliding engagement between the upper slide plate assembly and the lower slide plate assembly.

6. A limb restraining mechanism as claimed in claim 5, wherein tension biasing means connect the upper slide plate assembly to the lower slide plate assembly.

7. A limb restraining mechanism as claimed in claim 6, wherein handle means are affixed to the lower slide plate assembly by which the lower slide plate assembly is positioned with respect to the upper slide plate assembly.

8. A limb restraining mechanism as claimed in claim 7, wherein the distal end of the lower slide plate assembly terminates in a J shaped configuration.

* * * * *